(12) United States Patent
Koop et al.

(10) Patent No.: US 7,191,017 B1
(45) Date of Patent: Mar. 13, 2007

(54) TWO-PART IMPLANTABLE CARDIAC LEAD

(75) Inventors: Brendan E. Koop, Chanhassen, MN (US); Paul E. Zarembo, Vadnais Heights, MN (US)

(73) Assignee: Cardiac Pacemakers Inc., St. Paul, MN (US)

( * ) Notice: Subject to any disclaimer, the term of this patent is extended or adjusted under 35 U.S.C. 154(b) by 18 days.

(21) Appl. No.: 10/888,862

(22) Filed: Jul. 9, 2004

(51) Int. Cl.
*A61N 1/05* (2006.01)
(52) U.S. Cl. ...................... 607/122; 607/119
(58) Field of Classification Search ........ 607/122–123, 607/37, 115, 120; 439/909
See application file for complete search history.

(56) References Cited

U.S. PATENT DOCUMENTS

| | | | | |
|---|---|---|---|---|
| 4,332,259 A | * | 6/1982 | McCorkle, Jr. | 607/123 |
| 5,755,766 A | * | 5/1998 | Chastain et al. | 607/122 |
| 5,803,928 A | | 9/1998 | Tockman et al. | |
| 6,711,443 B2 | | 3/2004 | Osypka | |
| 6,895,277 B2 | * | 5/2005 | Westlund et al. | 607/37 |
| 6,915,169 B2 | * | 7/2005 | Flynn et al. | 607/122 |
| 6,921,295 B2 | | 7/2005 | Sommer et al. | |
| 2003/0074031 A1 | * | 4/2003 | Ley et al. | 607/37 |
| 2003/0143895 A1 | | 7/2003 | Sommer et al. | |
| 2003/0204231 A1 | | 10/2003 | Hine et al. | |
| 2005/0221671 A1 | * | 10/2005 | Lyu et al. | 439/587 |

\* cited by examiner

*Primary Examiner*—Robert E. Pezzuto
*Assistant Examiner*—Jessica L. Reidel
(74) *Attorney, Agent, or Firm*—Faegre & Benson LLP

(57) ABSTRACT

A two-part implantable cardiac pacing lead is usable with a cardiac function management device. The lead includes an outer lead portion having a lead body and a conductive coil extending substantially from the proximal end to the distal end. The lead body defines an internal longitudinal lumen. The lead further includes a surface electrode coupled to the lead body near the distal end and a sleeve defining an internal bore. The sleeve mechanically couples to the proximal end of the lead body and is electrically insulated from the conductive coil. The lead further includes an inner lead portion having a pin adapted to mechanically engage the internal bore. The pin is adapted for electrically coupling with a longitudinally-extending conductive member sized to fit within the internal longitudinal lumen.

28 Claims, 11 Drawing Sheets

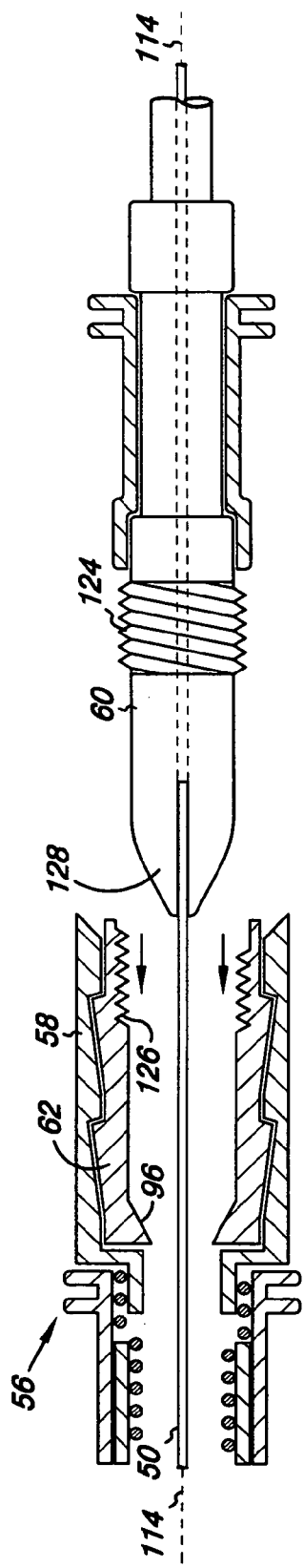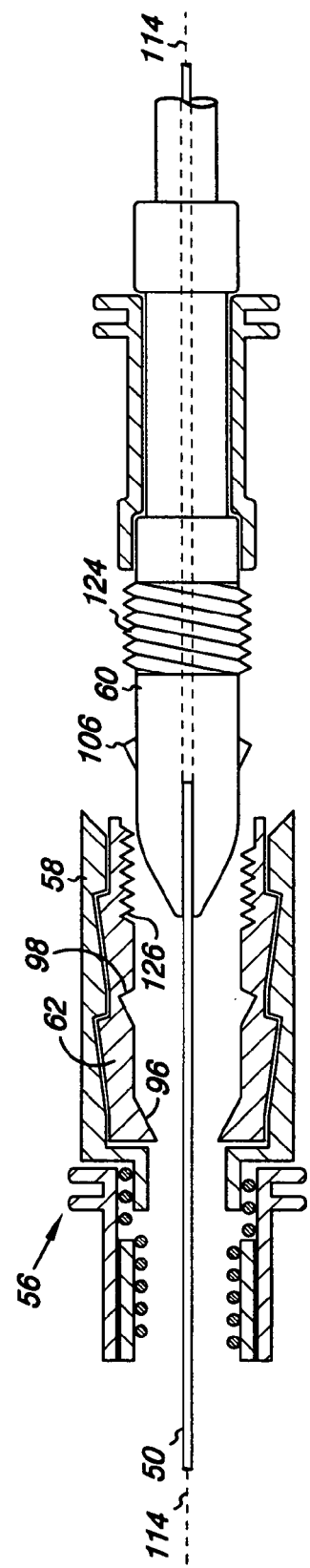

TWO-PART IMPLANTABLE CARDIAC LEAD

TECHNICAL FIELD

The present invention is related to implantable cardiac leads used with a cardiac function management device such as a pacemaker, a defibrillator, or a cardiac resynchronization therapy device to monitor and control heart function.

BACKGROUND

Cardiac function management devices, including implantable pacemakers and implantable defibrillators, include at least one cardiac lead having an electrode for making contact with a portion of the heart. Such leads are typically connected to a pulse generator at their proximal end and to cardiac tissue at their distal end. When such a lead is positioned so as to stimulate the left ventricle, it is common to advance the lead deep into the cardiac veins in order to effectively sense and stimulate in the left ventricle. However, traditional leads are not well suited for implantation in the coronary veins because the veins are narrow and traditional leads are often too large in diameter. Therefore, it is desirable to have a cardiac lead of a smaller size for placement in the coronary vein for left ventricle sensing and stimulation.

One such smaller size lead comprises a two-part bipolar lead where the first part of the lead includes an insulated conductive coil with an electrode at the distal end and the second part of the lead includes a wire or cable with an electrically conductive surface at its distal tip, which is delivered down the center of the conductive coil. There is a need in the art for a connector for such a lead that connects and secures the conductive cable to the conductive surface. There is a further need for such a device including a terminal connector compatible with standard cardiac function management devices.

SUMMARY

The present invention, according to one embodiment, is a cardiac lead for use with a cardiac function management device. The lead includes an elongated, flexible outer lead portion, the outer lead portion having a lead body, extending from a proximal end to a distal end, and a conductive coil extending substantially from the proximal end to the distal end, the lead body defining an internal longitudinal lumen. A first surface electrode is coupled to the lead body near the distal end. A terminal connector defining an internal bore and adapted to couple with the cardiac function management device is mechanically coupled to the proximal end of the lead body. An inner lead portion has a pin adapted to mechanically engage the internal bore. The pin is adapted for electrically coupling with a longitudinally-extending conductive member, which is sized to fit within the internal longitudinal lumen.

According to another embodiment, the present invention is a method of implanting a two-part bipolar cardiac lead in a coronary vein. The method includes positioning a guide catheter in the ostium of the coronary sinus and advancing an outer lead portion, having a longitudinal lumen and a terminal connector defining an internal bore and adapted to couple with a cardiac function management device at a proximal end, into the coronary sinus. An inner lead portion having a conductive member is provided, and the conductive member is advanced through the lumen. A pin is attached to a proximal end of the conductive member, such that the pin mechanically engages and couples to the internal bore of the terminal connector.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 6 is a partial sectional view of the proximal end and first portion of the cardiac lead of FIG. 2, wherein the pin is threadably engaged with the sleeve, according to a fourth embodiment of the present invention.

FIG. 7 is a partial sectional view of the proximal end and first portion of the cardiac lead of FIG. 2, according to a fifth embodiment of the present invention.

DETAILED DESCRIPTION

Figure 1:
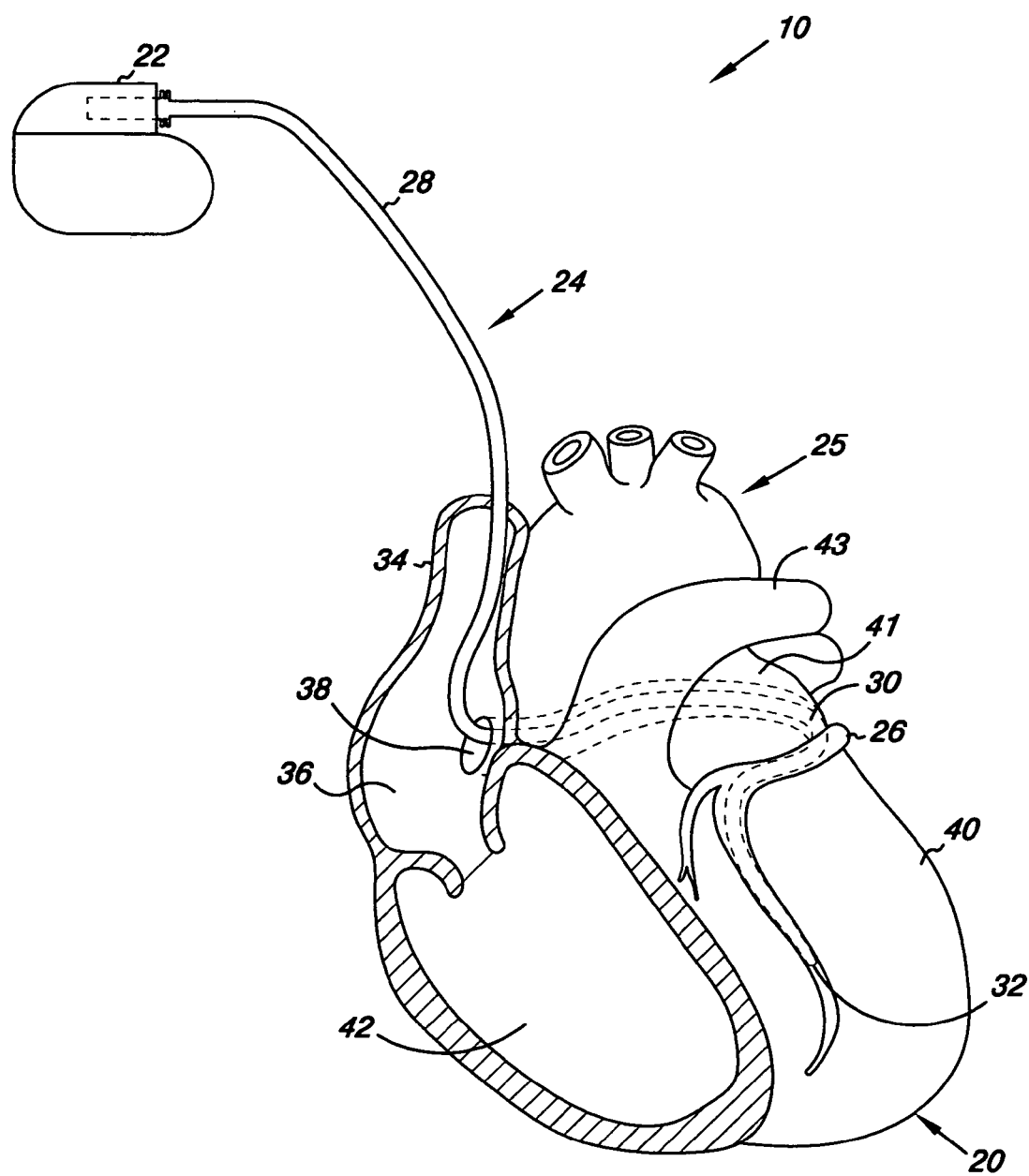
FIG. 1 is a perspective view of a cardiac function management system in accordance with the present invention.

FIG. 1 is a perspective view of a cardiac function management system 10 for delivering a treatment or therapy to a human heart. The cardiac function management system 10 may, for example, be a pacemaker, an ICD, or a cardiac resynchronization device. The system 10 includes a pulse generator 22 and a cardiac lead 24. The pulse generator 22 includes a power source, circuitry for receiving and delivering electrical signals through the cardiac lead 24, and circuitry for determining an appropriate therapy.

As shown in FIG. 1, the lead 24 is implanted into a human heart 25 through a coronary vein 26. The lead 24 operates to convey electrical signals between the heart 25 and the pulse generator 22. A proximal end 28 of the lead 24 is coupled to the pulse generator 22 and a distal end 30 includes to a surface electrode 32. In the embodiment shown in FIG. 1, the cardiac lead 24 of the present invention extends through the superior vena cava 34, the right atrium 36, and the coronary sinus 38 into the coronary vein 26, so that the surface electrode 32 is located in a branch of the coronary vein 26. When positioned as above, the electrode 32 can be used to sense the electrical activity of the heart 25 or to apply a stimulating pulse to the left ventricle 40. In other embodiments, the cardiac lead 24 of the present invention can also be implanted in any other portion of the heart as known in the art of cardiac function management. For example, it may be implanted in right atrium 36, the left atrium 41, the right ventricle 42, or the pulmonary artery 43.

Figure 2:
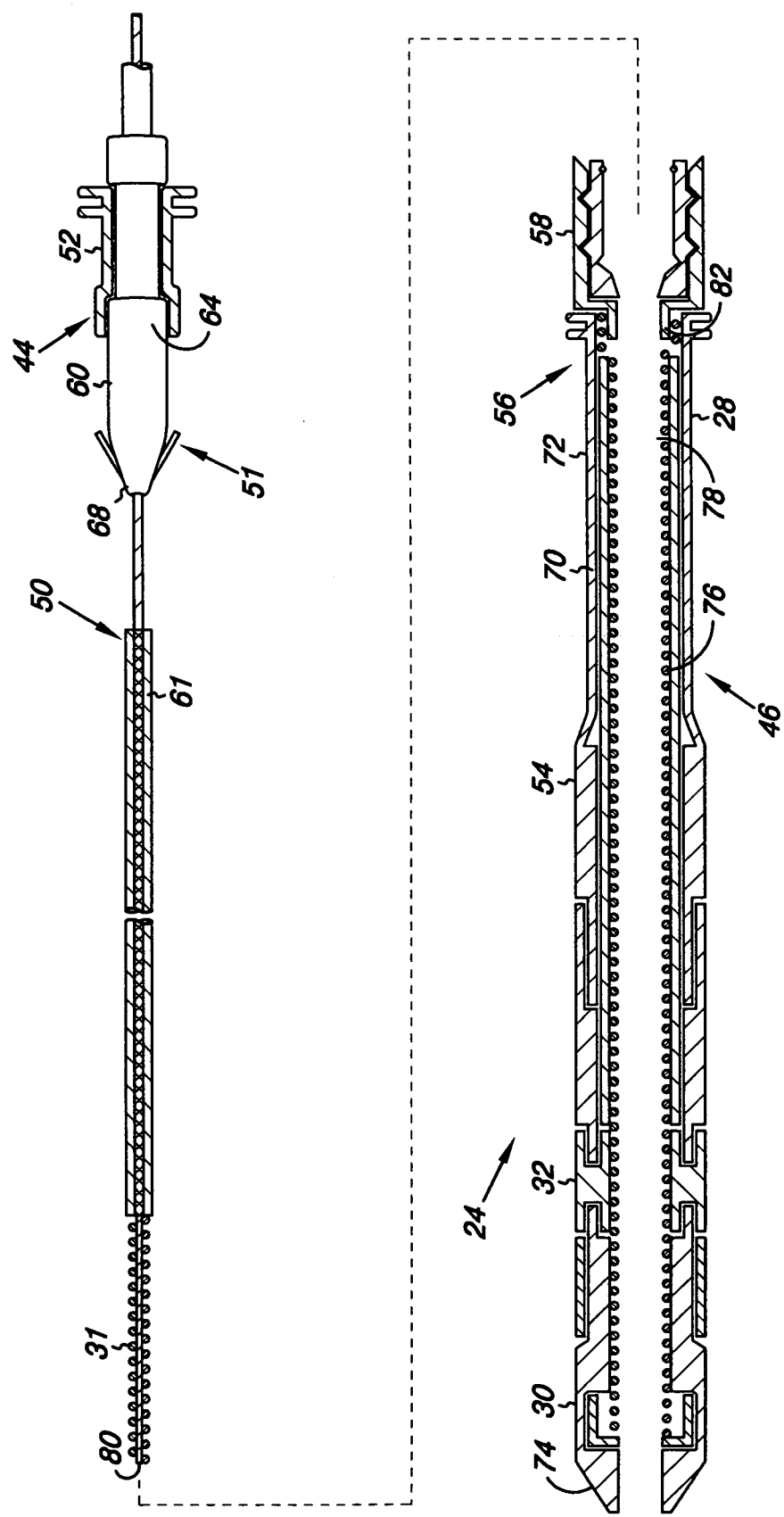
FIG. 2 is a sectional view of a cardiac lead of FIG. 1, according to one embodiment of the present invention.

FIG. 2 shows a sectional view of the cardiac lead 24 in accordance with the present invention. As shown in FIG. 2, the cardiac lead 24 includes an inner or first portion 44 and an outer or second portion 46. The first portion 44 is sized to fit into and couple with the second portion 46. The first portion 44, shown from left to right in FIG. 2, includes a conductive member 50, a connector assembly 51, and a front seal 52. As shown from left to right on the bottom portion of FIG. 2, the second portion 46 includes the surface electrode 32, a lead body 54, a rear seal 56, and a terminal connector 58.

The connector assembly 51 electrically and mechanically connects the cardiac lead 24 to the pulse generator 22. The connector assembly 51 includes a pin 60, which is configured to mechanically couple to the terminal connector 58 (or a tube or sleeve 62 as shown in FIGS. 3–8). The pin 60, which is made from an electrically conductive material, is adapted to connect electrically and mechanically to the cable or conductive member 50. The connection can be preformed or formed upon coupling with the terminal connector 58. In embodiments where the connection is formed upon coupling with the terminal connector 58, the connection can be permanent or reversible. The pin 60, however, is electrically insulated from the terminal connector 58. In one embodiment, the conductive member 50 is a wire or a cable. The conductive member 50 may include an insulating sheath 61. The insulating sheath 61 can be a polymer or other insulating material surrounding the conductive member 50. As shown in FIG. 2, the front seal 52 surrounds a proximal end 64 of the pin 60. The front seal 52 is a standard seal as is known in the industry, such as an IS-1 seal. The front seal 52 may have any other standard terminal configuration known in the art.

The lead body 54 of the second portion 46 is sized to allow cannulation of the coronary sinus and coronary veins. The lead body 54 includes an outer sheath 70 that substantially extends from a proximal end 72 of the lead body 54 to a distal end 74 of the lead body 54 and can be made of polyurethane tubing or any other material known in the art. The outer sheath 70 encapsulates a flexible conductive coil 76. In one embodiment, the outer sheath 70 encapsulates one or more cables or both cables and a conductive coil 76. In one embodiment, the conductive coil 76 may be coated with any biocompatible, polymeric material, such as, for example, ETFE, PTFE, silicone rubber, or polyurethane. In various embodiments the conductive coil 76 is made from any biocompatible material, such as stainless steel, MP35N, Platinum/Tantalum, and DFT.

A lumen 78 is located inside the lead body 54 and extends from the proximal end 72 to the distal end 74. Upon assembly of the first portion 44 and the second portion 46, the conductive member 50 extends through the lumen 78 from the proximal end 28 of the cardiac lead 24 to near the distal end 30 of the cardiac lead 24. In one embodiment, the conductive member 50 extends beyond the distal end 30 and has a tip 80 serving as an electrode 31. The conductive member 50 can be used convey sense electrical activity from the heart 25 or to convey electrical signals to the heart 25, or both. Alternatively, the conductive member 50 may not extend beyond the distal end 30 of the cardiac lead 24, but instead may couple to an electrode on the lead body 54 (see, for example, FIGS. 11B and 11C.) In one embodiment, a spiral fixation shape is incorporated into the distal end 74 of the lead body 54, which can facilitate fixation of the lead inside of the coronary vein. In another embodiment, fixation is accomplished using tines coupled to the distal end 74 of the lead body 54.

The terminal connector 58, as shown in FIG. 2, includes a tab 82 that is inserted into the proximal end 72 of the lead body 54. The tab 82 of the terminal connector 58 is electrically connected to the conductive coil 76. The rear seal 56 surrounds a portion of the conductive coil 76 that overlaps with the tab 82. The surface electrode 32 is located at the distal end 30 of the cardiac lead 24. The surface electrode 32 can be a terminal connector electrically connected to the conductive coil 76 or alternatively can be created by removing an annular portion of outer sheath 70, thus exposing a portion of conductive coil 76. The position of the surface electrode 32 along the cardiac lead 24 can vary. In one embodiment, the lead 24 includes more than one surface electrode 32.

Figure 3:
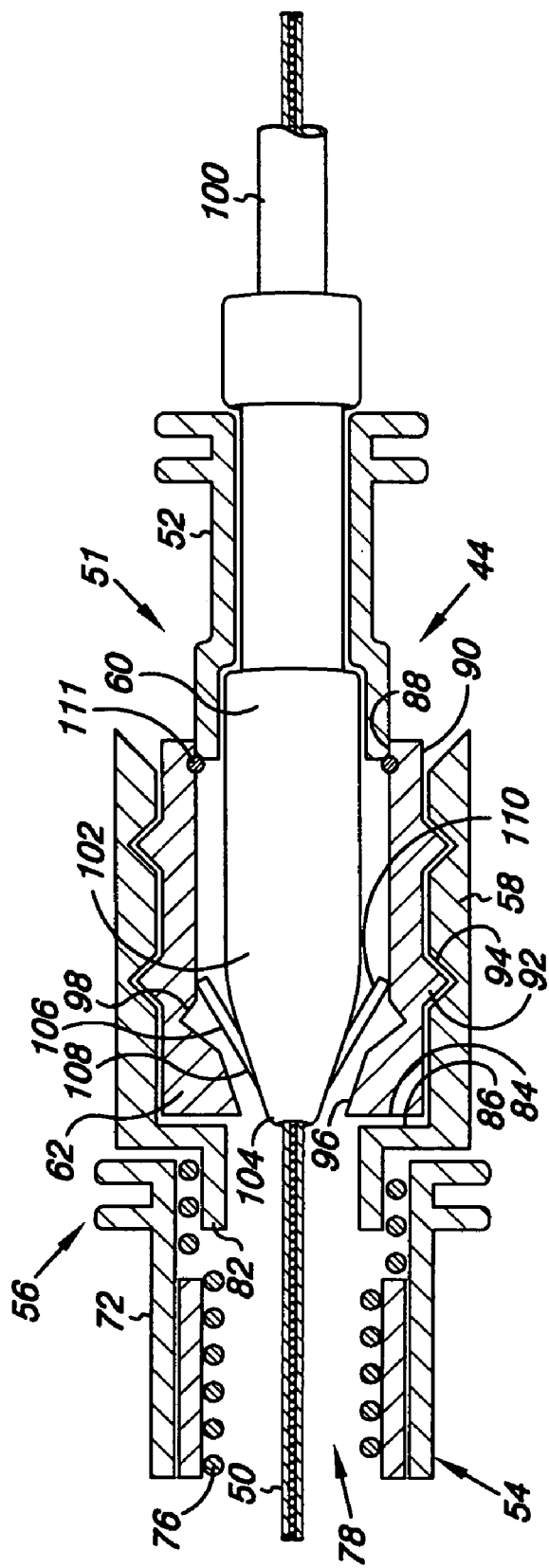
FIG. 3 is a partial sectional view of the proximal end and first portion of the cardiac lead of FIG. 2, according to one embodiment of the present invention.

FIG. 3 shows a partial sectional view of the proximal end 72 of the lead body 54 and the first portion 44 of the cardiac lead 24, in accordance with one embodiment of the present invention. As shown in FIG. 3, the first portion 44 includes the conductive member 50, the connector assembly 51, and the front seal 52. The connector assembly 51 includes the pin 60, which is adapted for insertion into the sleeve 62. The sleeve 62 is generally shaped like a hollow cylinder and is adapted for insertion into and coupling with the terminal connector 58. The sleeve may be formed, for example, for PEEK, tecothane, or other biocompatible polymers. In one embodiment, the sleeve 62 is adapted to snap fit into the terminal connector 58. In another embodiment, the sleeve 62 is formed directly on the interior surface of the terminal connector 58. In another embodiment, the sleeve 62 is formed directly on the pin 60.

As shown in FIG. 3, the sleeve 62 includes a leading surface 84 which contacts a shoulder 86 of the terminal connector 58 when the sleeve 62 is inserted into the terminal connector 58. The sleeve 62 also includes an inner surface 88 and an outer surface 90. The outer surface 90 has protrusions 92, which mate with indentations 94 on the terminal connector 58. The protrusions 92 encircle the sleeve 62 and fit into the grooves comprising the indentations 94 on the terminal connector 58. The protrusions 92 and indentations 94 could be of any configuration that effects mechanical coupling between the sleeve 62 and the terminal connector 58. The inner surface 88 of the sleeve 62 has an angled surface 96, which forms a triangular groove within the sleeve 62. The inner surface 88 of the sleeve 62 also has indentations 98 adapted for mating with the pin 60. The indentations 98 could be grooves or any other receptive feature as is known in the art.

The pin 60 has a generally cylindrical shape and has a pin proximal end 100, a pin distal end 102, a pin tip 104, and pin protrusions 106. As shown in FIG. 3, the pin distal end 102 is tapered. In an alternative embodiment, the pin distal end 102 need not be tapered. The pin distal end 102 is electrically and mechanically connected or coupled to the conductive member 50. The pin protrusions 106 have an attaching end 108 and an engaging end 110 and are interposed between the pin tip 104 and the pin proximal end 100. The attaching end 108 is resiliently attached to the pin 60 so that the pin protrusions 106 are compressed toward the pin 60 as the pin 60 is inserted into the sleeve 62 and expand outward into the indentations 98 upon reaching the indentations 98, thereby locking the pin 60 into place in the sleeve 62. The embodiment of FIG. 3 shows two protrusions 106 but any number of protrusions could be used. In an alternative embodiment, pin protrusions 106 could be one or more solid protrusions encircling the pin 60, or the pin protrusions 106 could be some other attachment feature as is known in the art, such as leaf springs. In one embodiment, the sleeve 62 (or terminal connector 58) supports a seal 111 near the proximal end. In this embodiment, the seal 111 functions to contact a leading portion of the front seal 52, such that when the first portion 44 is inserted into the second portion 46, the two portions form a sealed interface.

Figure 4A:
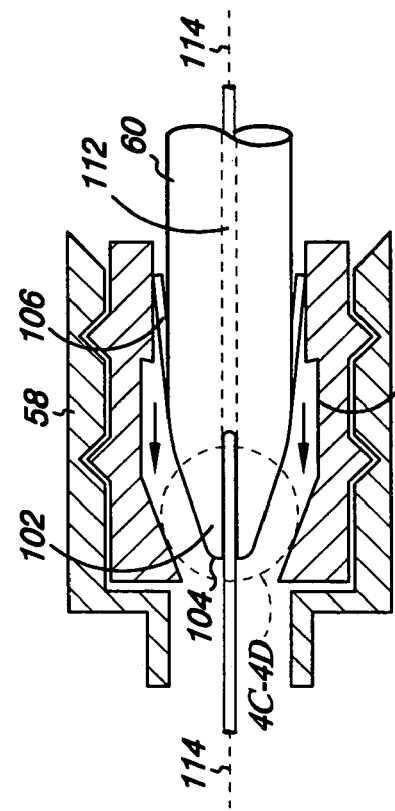
FIGS. 4A–4B are partial sectional views of the proximal end and first portion of the cardiac lead of FIG. 2, according to another embodiment of the present invention.
Figure 4B:
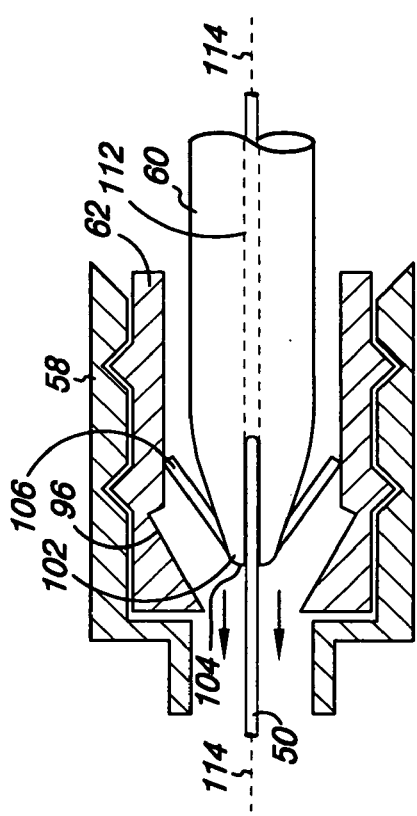

FIGS. 4A–4B show partial sectional views of the interface between the pin 60 of the first portion 44 and the terminal connector 58 of the second portion 46. In one embodiment, the conductive member 50 is fixed with respect to the pin 60, such that the pin 60 and the conductive member 50 are inserted into the second portion 46 simultaneously. In another embodiment, the pin 60 is adapted for insertion over the conductive member 50, after the conductive member 50 is properly positioned within the second portion 46. As shown in FIG. 4A, the pin 60 includes a lumen 112 extending along the longitudinal axis 114 of the pin 60. The conductive member 50 is positioned in the lumen 112. The pin engages with the sleeve 62, locking the pin 60 and the conductive member 50 into place. In the embodiment shown in FIG. 4A, pin protrusions 106 are attached at the pin distal end 102. In the alternative embodiment shown in FIG. 4B, the pin protrusions 106 are attached at a location further from the pin tip 104.

Figure 4C:
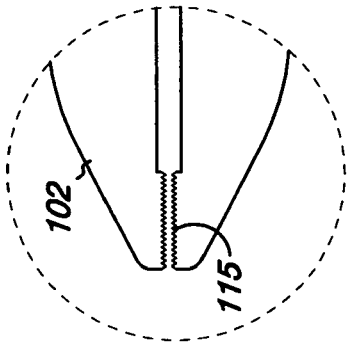
FIGS. 4C–4D show side plan view of the portion of FIG. 4B indicated as 4C–4D.
Figure 4D:
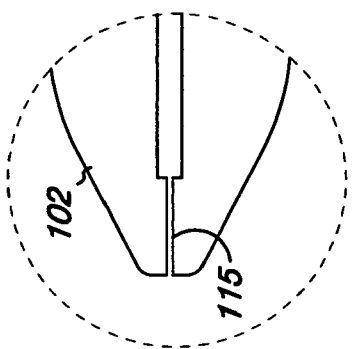

FIGS. 4C and 4D show side views of the portion of FIG. 4B marked 4C–4D. FIGS. 4C and 4D show the jaws 102 in further detail. As shown, as the jaws 102 close, they cut through the insulating sheath 61 thereby creating both a mechanical and an electrical connection between the pin 60 and the conductive member 50. In the embodiment shown in FIG. 4C, the jaws 102 include substantially flat edges 115 for cutting through the insulating sheath 61. In another embodiment shown in FIG. 4D, the jaws 128 have serrated edges 115. In this embodiment, the pin tip 104 may be composed of 2, 3, 4, or more jaw members 102.

Figure 5A:
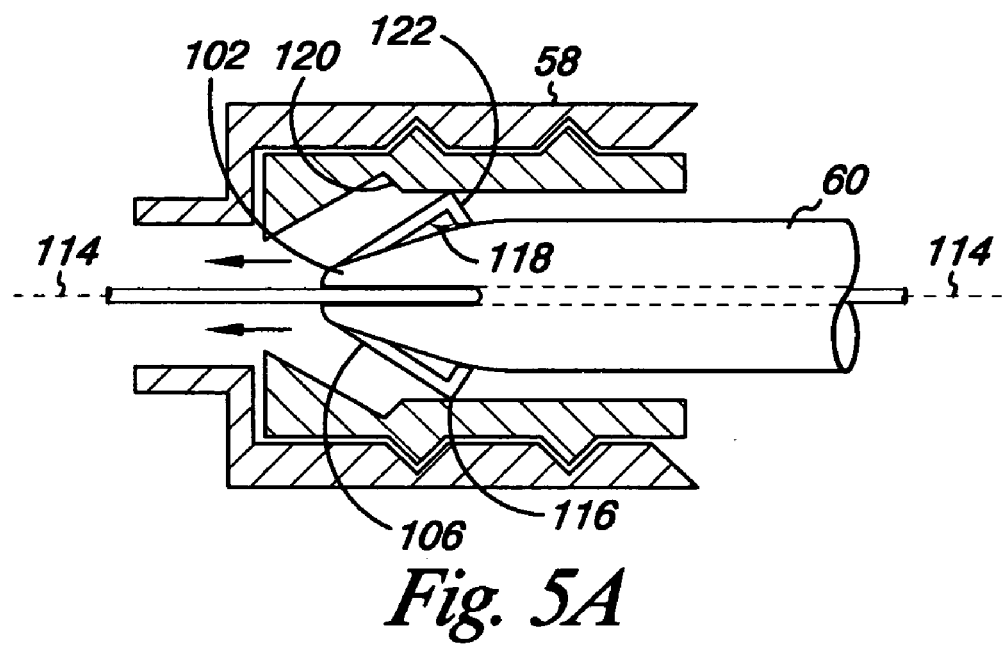
FIGS. 5A–5B are partial sectional views of the proximal end and first portion of the cardiac lead of FIG. 2, according to a third embodiment of the present invention.
Figure 5B:
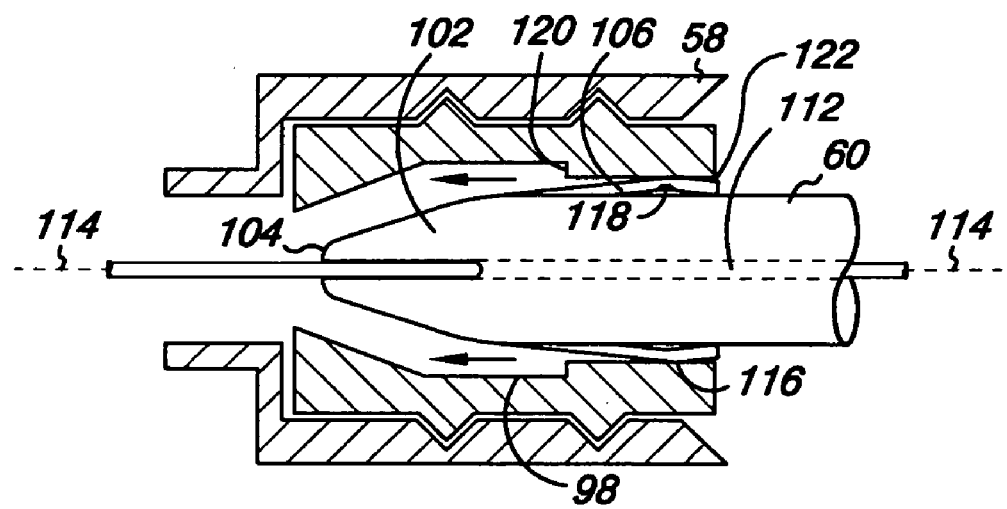

FIGS. 5A–5B show partial sectional views of the interface between the pin 60 of the first portion 44 and the terminal connector 58 of the second portion 46, wherein the pin 60 is removably coupled to the sleeve 62. As shown in FIG. 5A, the pin protrusions 106 include a bend having an angle 118. The angle 118 is such that when the pin 60 is pulled out of the sleeve 62, a contact area 120 acts against a top surface 122 of the protrusion 106 to compress the protrusion 106 toward the pin 60, thereby releasing the pin 60 from the sleeve 62 and allowing removal of the pin 60 and repositioning of the conductive member 50. In the embodiment shown in FIG. 5A, the pin protrusions 106 are attached at the pin distal end 102. In the alternative embodiment shown in FIG. 5B, the pin protrusions 106 are attached at a position further from the pin tip 104.

FIG. 6 shows a partial sectional view of an alternative embodiment of the present invention, wherein the conductive member 50 is removable from the pin 60. As shown in FIG. 6A, the pin 60 is threadably engagable with the sleeve 62. In the embodiment shown in FIG. 6A, the pin 60 has external threads 124 and the sleeve 62 has mating internal threads 126. When the pin 60 is screwed into the sleeve 62, a leading angled surface 96 of jaws 128 contact the angled surface 96, which causes the jaws 128 to close on the conductive member 50.

FIG. 7 shows a partial sectional view of yet another alternative embodiment of the present invention. As shown in FIG. 7, the pin 60 includes both threads 124 and protrusions 106. The sleeve 62 includes the sleeve inner surface indentations 98 and threads 126. In the embodiment shown in FIG. 7, the protrusions 106 are shaped in the form of a chamfer so that as the pin 60 is screwed into the sleeve 62, the protrusions 106 mechanically engage with the sleeve inner surface indentations 98, locking the pin 60 into place in sleeve 62. In an alternative embodiment, the pin 60 and sleeve 62 include pin protrusions 106 and sleeve inner surface indentations 98 of the type shown in FIGS. 3–5B. The location of the protrusions 106 and inner sleeve indentations 98 can vary along the longitudinal axis 114.

Figure 8:
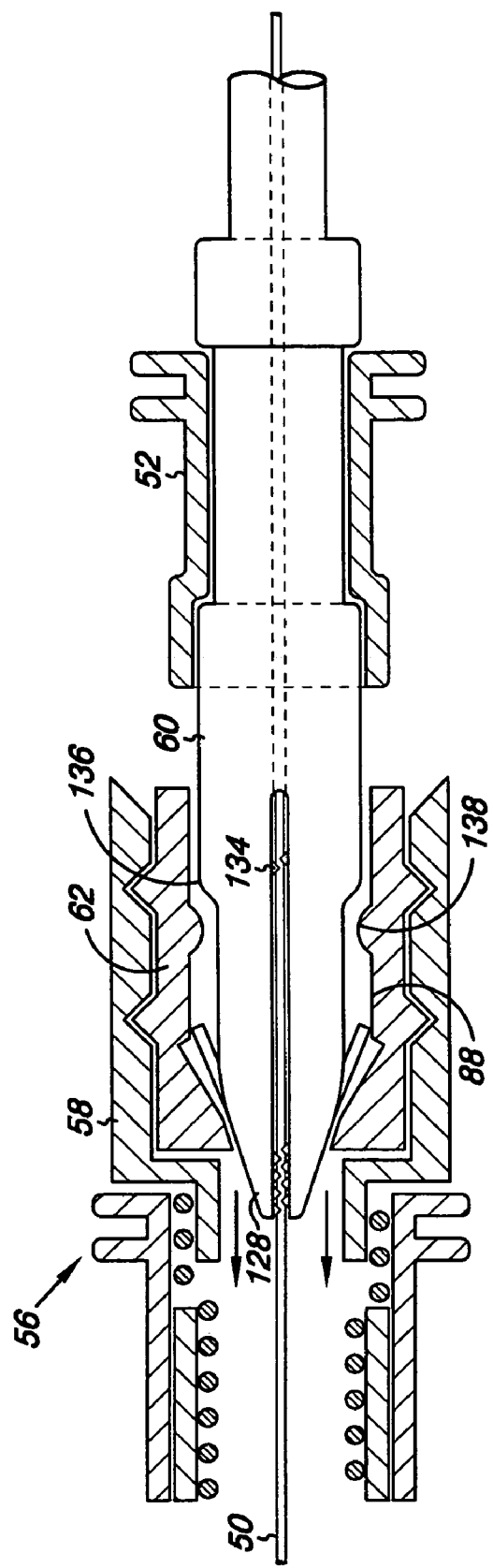
FIG. 8 is a partial sectional view of the proximal end and first portion of the cardiac lead of FIG. 2, according to a sixth embodiment of the present invention.

FIG. 8 shows a partial sectional view of yet another alternative embodiment of the present invention, wherein the pin 60 and the sleeve 62 act to sever the conductive member 50 when the pin 60 is mechanically engaged with the sleeve 62. As shown in FIG. 8, the pin 60 includes cutting edges 134 and a shoulder 136. The sleeve 62 includes a protrusion 138. The shoulder 136 and protrusions 138 are located at a distance along the longitudinal axis 114 such that when the shoulder 136 reaches the protrusions 138, the protrusions 138 act against the shoulder 136, causing the cutting edges 134 to compress, thereby severing the conductive member 50. In the embodiment shown in FIG. 8, the protrusions 138 have an arcuate shape, but other shapes are within the scope of the present invention, including a chamfer encircling the inner surface 88 of the sleeve 62. The number of protrusions 138 and cutting points 134 can also vary as needed.

Figure 9A:
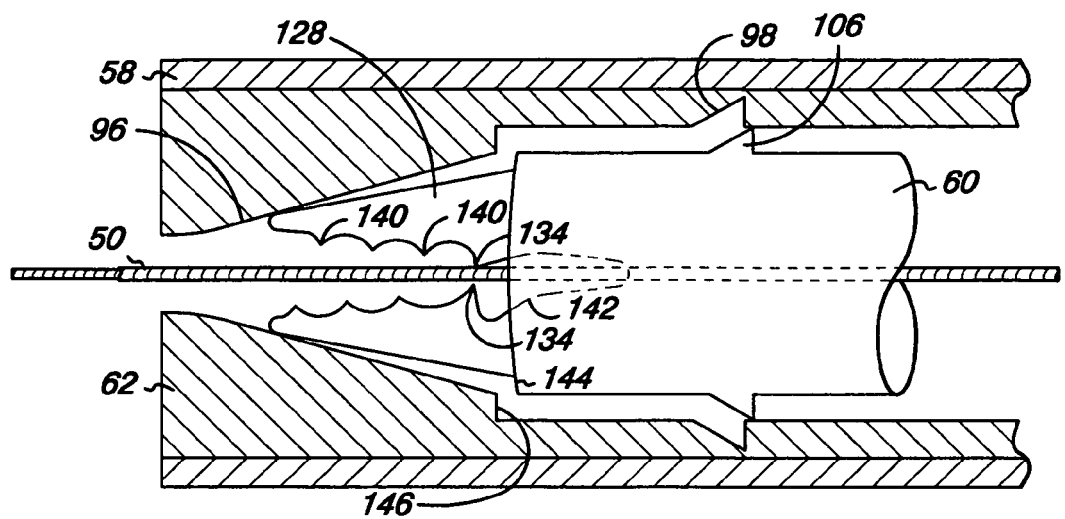
FIGS. 9A–9C are various views of the proximal end and first portion of the cardiac lead of FIG. 2, according to a seventh embodiment of the present invention.
Figure 9B:
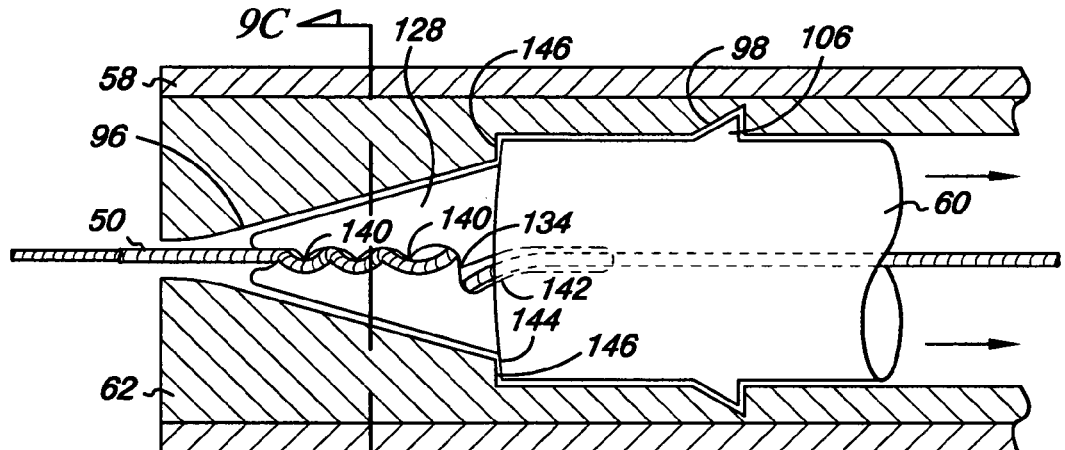
Figure 9C:
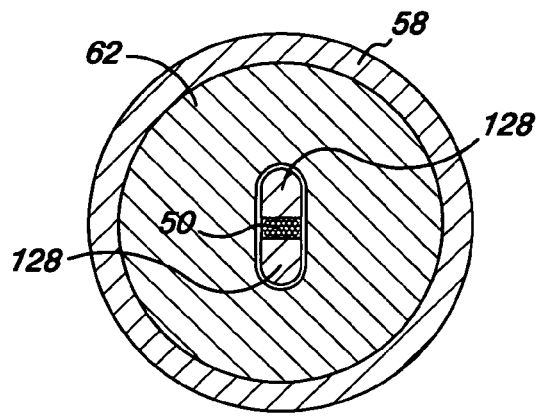

FIGS. 9A–9B show an alternative embodiment of the present invention wherein the jaws 128 include cutting points 134, gripping points 140 and a jaw indentation 142. The cutting points could be made using any technique known in the art, including, for example, wire EDM. The pin 60 includes a leading surface 144 and the sleeve 62 includes a shoulder 146. In this embodiment, as the pin 60 is advanced into the sleeve 62, the angled surface 96 acts to compress the jaws 128 together. As the jaws 128 are compressed together, gripping points 140 retain the conductive member 50 in the jaws 128 and cutting points 134 sever the conductive member 50. In one embodiment, as shown in FIG. 9C, the jaws 128 act in conjunction with the sleeve 62 to constrain the cable or conductive member 50, such that when it is gripped by gripping points 140 or cut at cutting points 134, the cable does not flatten, which would impede this gripping or cutting action.

The conductive member 50 is forced into the jaw indentation 142 and can then be removed from the pin 60 in the direction shown by the arrow in FIG. 9B. When the pin 60 is inserted into the sleeve 62, the leading surface 144 contacts the sleeve shoulder 146 to stop the pin from advancing further into the sleeve 62. In the embodiment shown in FIGS. 9A–9B, pin protrusions 106 mechanically engage with sleeve inner surface indentations 98 to lock the pin 60 into place. Alternatively, the pin 60 and sleeve 62 could be threadably engaged as shown in FIGS. 6A–6C, or engaged using threads and a snap fit as shown in FIG. 7.

Figure 10A:
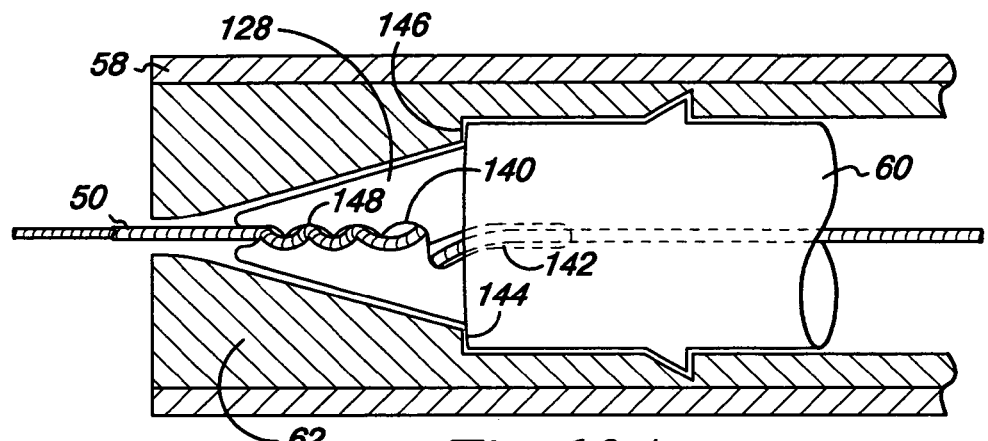
FIGS. 10A–10C are partial sectional views of the jaws of FIGS. 9A–9B, wherein the jaws include mechanisms for gripping the conductive member, according to alternative embodiments of the present invention.
Figure 10B:
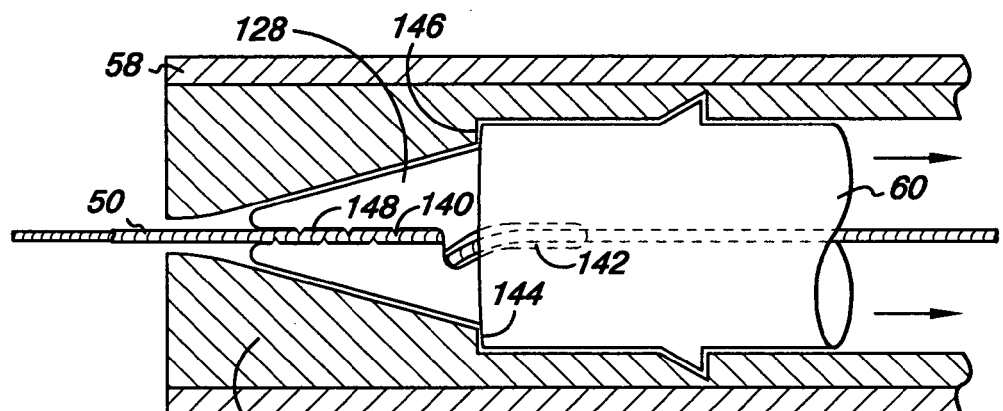
Figure 10C:
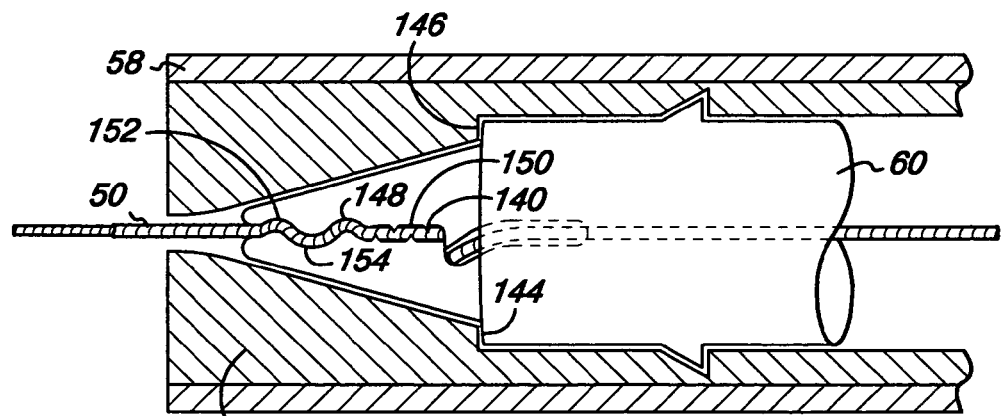

FIGS. 10A–10C show alternative embodiments of the jaw gripping mechanism. In FIG. 10A, the jaws 128 have inner surfaces 148 having sinusoidal shapes and gripping points 140 that are sharp enough to cut through the insulating sheath 61 of the conductive member 50. In FIG. 10B, the inner surfaces 148 are substantially flat so as to better control the depth of the cut into the insulating sheath 61. In the embodiment shown in FIG. 10C, the inner surfaces 148 have a proximal end 150 and a distal end 152. The proximal end 150 includes gripping points 140 that cut through the insulating sheath 61. The distal end 152 includes curves 154 that act to hold the conductive member 50 into place without penetrating the insulating sheath 61.

Figure 11A:
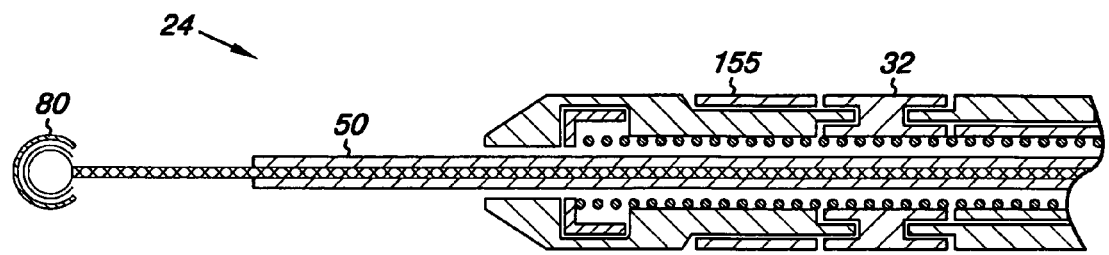
FIGS. 11A–11C are sectional views of the distal end of the cardiac lead of FIG. 2, according to yet other alternative embodiments of the present invention.
Figure 11B:
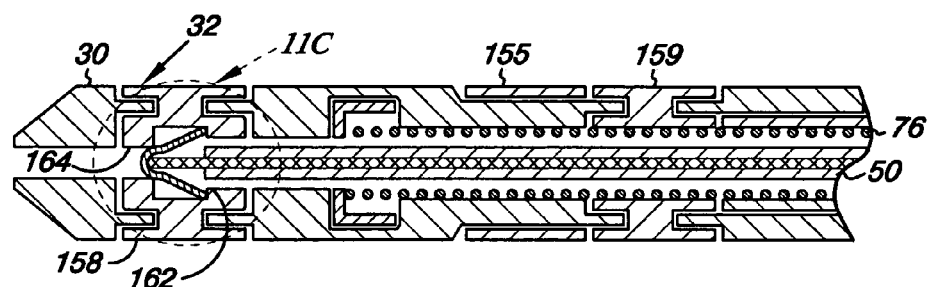
Figure 11C:
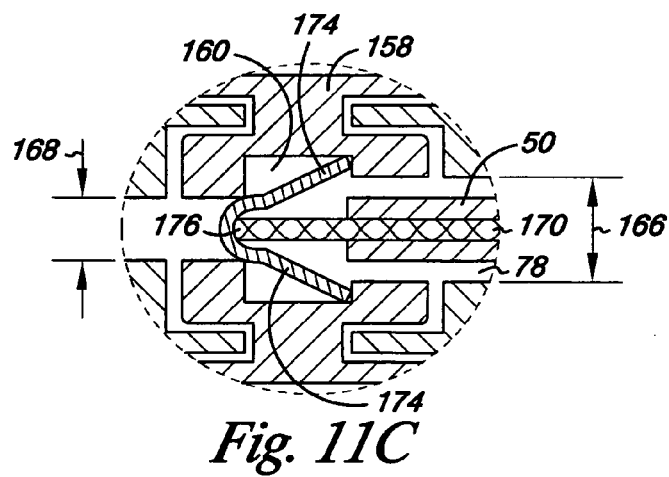

FIGS. 11A–11C show alternative embodiments of the distal end of the cardiac lead 24. In the embodiment shown in FIG. 11A, the conductive member 50 extends beyond the distal end 30 of the lead body 54. The conductive member 50 has a generally spherically-shaped tip 80. The tip 80 can also be canted or biased to one side to improve contact with the coronary vein 26. In this embodiment, the tip 80 of the conductive member 50 functions as the surface electrode 31. In one embodiment, the lead body further includes a drug collar 155.

In an alternative embodiment shown in FIGS. 11B and 11C, the surface electrode 32 includes a first surface electrode 158 located near the distal end 30 of the cardiac lead 24 and a second surface electrode 159 located further from the distal end 30. As shown in FIG. 11C, the first surface electrode 158 includes recesses 160, a proximal surface 162, and a distal surface 164. The proximal diameter 166 is slightly larger than the distal diameter 168 so that the conductive member 50 can pass through the proximal diameter 166 but not the distal diameter 168. The distal diameter 168 is large enough that a guidewire (not shown) can pass through it.

As further shown in FIG. 11C, the conductive member 50 includes a cable conductor 170 and tines 174. As shown in FIG. 11C, the tines 174 are resiliently attached to the tip 176 of the cable conductor 170. When the conductive member 50 is inserted through the lumen 78 of the lead body 54 sufficiently far that the tines 174 reach the recesses 160, the tines 174 expand outward into the recesses 160, thereby electrically and mechanically attaching to the surface electrode 158. Two tines 174 are shown in FIG. 11B, but any number could be used as needed for retention properties. In this embodiment, the conductive member 50 can be used to electrically couple the first surface electrode 158 to the pin 60. In other embodiments, any other configuration known in the art can be used to couple the distal end of the conductive member to either of the surface electrodes 158, 159. In one embodiment, the conductive member 50 is fixed with respect to the lead body 54, such that the conductive member 50 can be used as a stylet for delivering the lead body 54. In one embodiment, the conductive member 50 is fixed rotationally, such that it can be used to apply torque for steering the lead body 54 during delivery. In one such embodiment, the conductive member 50 has a pre-formed shape to assist in delivery and cannulation.

Figure 12:
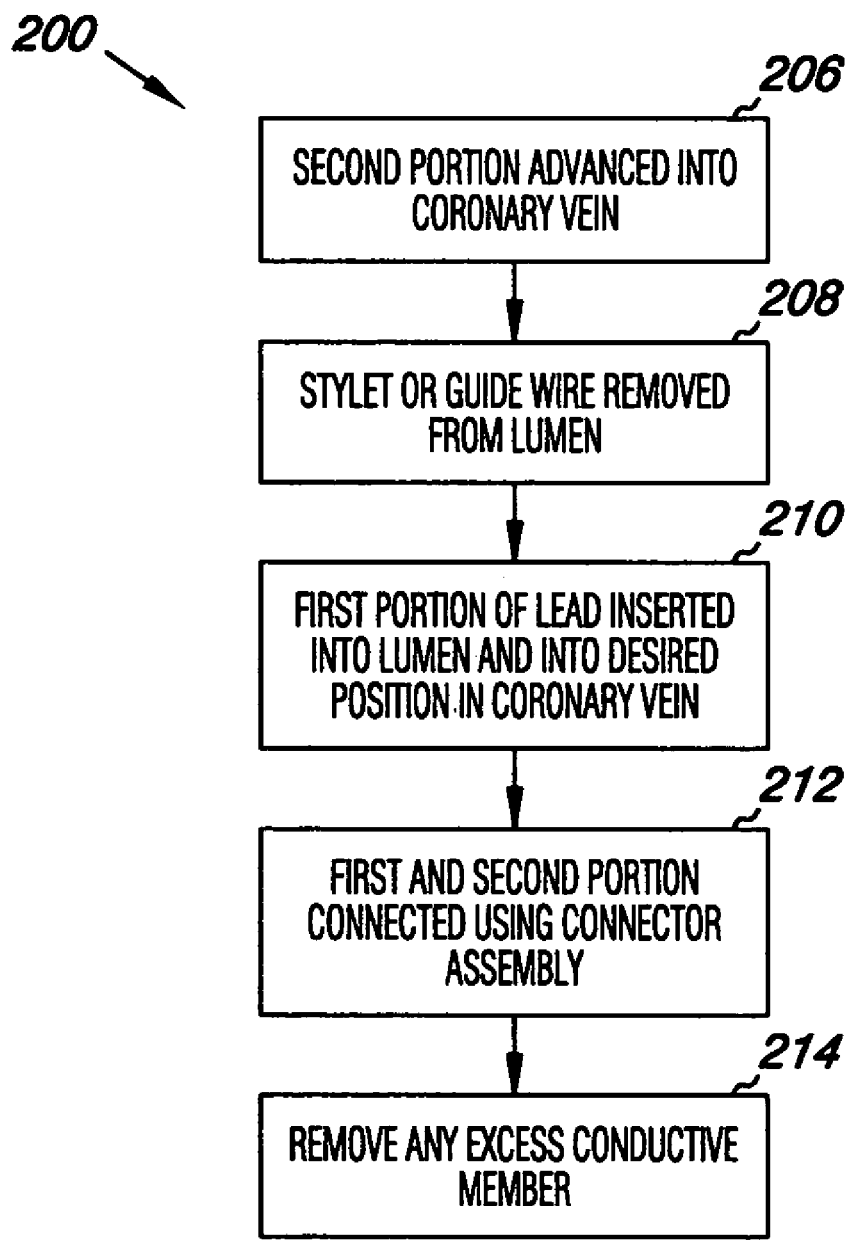
FIG. 12 is a flowchart showing an implantation process for implanting the cardiac lead of FIG. 2 into the human heart.

FIG. 12 depicts an exemplary implantation process 200 for implanting the cardiac lead 24 into the human heart 25. As shown, the second portion 46 of the cardiac lead 24 is advanced, using a stylet or over a guide wire, to the desired position in the coronary vein 26 (block 206). In one embodiment, the cardiac lead 24 is advanced through a previously-placed guide catheter extending through the vasculature to the coronary sinus. The stylet or guide wire is then removed from the lumen 78 of the second portion 46 (block 208). Next, the first portion 44 of the cardiac lead 24 is inserted into the lumen 78 and advanced to the desired position in the coronary vein 26 (block 210). The conductive member 50 is then advanced through a lumen in the first portion 44. In one embodiment, the conductive member 50 is advanced to a position extending beyond the distal end of the lead body 54, such that the tip 80 can act directly as a surface electrode 31 (see FIG. 11A). In another embodiment, the distal end of the conductive member 50 couples to a surface electrode 32 located on the lead body 54 (see FIGS. 11B–11C). The first portion 44 and the second portion 46 are then connected using the connector assembly 51 at the proximal end 28 of the cardiac lead 24 (block 212). If needed, any excess portion of the conductive member 50 can be removed (block 214). In an alternative embodiment, the connector assembly 51 is pre-affixed to the conductive member 50, such that insertion of the conductive member 50 and coupling of the connector assembly 51 to the second portion 46 occur simultaneously. In yet another alternative method, the conductive member 50 can be used as a stylet to deliver the second part 46 of the cardiac lead 24.

Although the present invention has been described with reference to exemplary embodiments, persons skilled in the art will recognize that changes may be made in form and detail without departing from the spirit and scope of the invention.

We claim:

1. A two-part cardiac lead for use with a cardiac function management device, the lead comprising:
   an elongated, flexible outer lead portion including a lead body extending from a proximal end to a distal end and defining an internal longitudinal lumen, a conductive coil extending substantially from the proximal end to the distal end, a surface electrode coupled to the lead body near the distal end, a conductive terminal connector defining an internal bore and adapted to couple with the cardiac function management device, the conductive terminal connector coupled to the proximal end of the lead body, and a sleeve located in the internal bore and having an indentation; and
   an inner lead portion including a longitudinally-extending conductive member sized to fit within the internal longitudinal lumen and a pin having a protrusion sized to mechanically couple with the sleeve indentation, the pin adapted to electrically couple with the longitudinally-extending conductive member;
   wherein the sleeve is adapted to electrically isolate the pin from the conductive terminal connector.

2. The cardiac lead of claim 1 wherein the conductive member has a length such that, when the pin is mated with the conductive terminal connector, the conductive member extends beyond the distal end of the lead body.

3. The cardiac lead of claim 2 wherein a distal end of the conductive member includes a conductive tip.

4. The cardiac lead of claim 1 wherein the conductive terminal connector includes an interior recess and the sleeve includes an exterior protrusion sized to mate with the interior recess, to couple the sleeve to the conductive terminal connector.

5. The cardiac lead of claim 1 wherein the protrusion is a finger comprising an attachment end and an engaging end and wherein the finger attachment end is resiliently attached to a distal end of the pin, and wherein the finger is adapted to expand outward and mechanically engage with the sleeve indentation as the pin is inserted into the sleeve.

6. The cardiac lead of claim 5 wherein the finger includes at least one bend and a contact area so that when the pin is removed from the sleeve, the sleeve indentation acts against the contact area, thereby compressing the finger toward the pin and releasing the pin from the sleeve.

7. The cardiac lead of claim 1 wherein the protrusion is in the shape of a chamfer and wherein the sleeve indentation is sized to mate with the chamfer.

8. The cardiac lead of claim 1 wherein the protrusion comprises external threads and wherein the sleeve indentation comprises internal threads adapted to mate with the external threads.

9. The cardiac lead of claim 1 wherein the pin further includes a lumen extending from a pin proximal end to a pin distal end.

10. The cardiac lead of claim 9 wherein the conductive member is disposed in the pin lumen and is mechanically fixed with respect to the pin.

11. The cardiac lead of claim 9 wherein the conductive member is slideably disposed in the pin lumen.

12. The cardiac lead of claim 11 wherein the pin farther includes jaws at the pin distal end, the jaws having inner surfaces, and wherein the internal bore is tapered at a sleeve distal end such that the pin jaws are compressed toward the conductive member, when the pin is disposed in the sleeve.

13. The cardiac lead of claim 11 wherein the pin lumen includes severing edges and wherein the sleeve includes a sleeve bore having protrusions adapted to compress the pin lumen as the pin is inserted into the sleeve so that the pin severing points sever the conductive member.

14. The cardiac lead of claim 1 wherein the surface electrode includes at least one recess and the conductive member includes a cable conductor and at least one tine adapted for mechanically and electrically coupling with the at least one recess.

15. A two-part cardiac lead for use with a cardiac function management device, the lead comprising:
an outer lead portion having a lead body extending from a proximal end to a distal end and defining a lumen, a conductive coil extending substantially from the proximal end to the distal end, an electrode coupled to the lead body, and a conductive terminal connector defining an internal bore, coupled to the proximal end of the lead body, and including a first feature; and
a separable inner lead portion having a conductive member sized to fit within the lumen and a pin including a second feature sized to engage the first feature, the pin adapted for electrically coupling with the conductive member.

16. The cardiac lead of claim 15 wherein the conductive member has a length such that, when the pin is mated with the conductive terminal connector, the conductive member extends beyond the distal end of the lead body.

17. The cardiac lead of claim 15 wherein a distal end of the conductive member includes a conductive tip.

18. The cardiac lead of claim 15 wherein the pin further includes a lumen extending from a pin proximal end to a pin distal end and the conductive member is slideably disposed in the pin lumen.

19. The cardiac lead of claim 15 wherein the conductive member is mechanically fixed with respect to the pin.

20. The cardiac lead of claim 15 wherein the electrode includes at least one recess and the conductive member includes a cable conductor and at least one tine adapted for mechanically and electrically coupling with the at least one recess.

21. A two-part cardiac lead for use with a cardiac function management device, the lead comprising:
an outer lead portion having a lead body extending from a proximal to a distal end and defining a lumen, an electrode coupled to the lead body, a conductive coil extending from the proximal to the distal end, a conductive terminal connector located at the proximal end, and a sleeve located within the conductive terminal connector; and
a separable inner lead portion having a conductor and a pin, the pin including a means for engaging the sleeve;
wherein the pin is adapted to mechanically couple to the proximal end of the lead body.

22. The lead of claim 21 wherein the conductor has a length such that, when the pin is coupled with the sleeve, the conductor extends beyond the distal end of the lead body.

23. The lead of claim 21 wherein a distal end of the conductor includes a conductive tip.

24. The lead of claim 21 wherein the electrode includes at least one recess and the conductor includes a cable conductor and at least one tine adapted for mechanically and electrically coupling with the at least one recess.

25. The lead of claim 21 wherein the pin further includes a lumen extending from a pin proximal end to a pin distal pin.

26. The lead of claim 25 wherein the conductor is disposed in the pin lumen and is mechanically fixed with respect to the pin.

27. The lead of claim 25 wherein the conductor is slideably disposed in the pin lumen.

28. The lead of claim 21 wherein the means for engaging the sleeve is releasable.

* * * * *

UNITED STATES PATENT AND TRADEMARK OFFICE
CERTIFICATE OF CORRECTION

PATENT NO. : 7,191,017 B1 Page 1 of 1
APPLICATION NO. : 10/888862
DATED : March 13, 2007
INVENTOR(S) : Brendan E. Koop et al.

It is certified that error appears in the above-identified patent and that said Letters Patent is hereby corrected as shown below:

<u>Column 9</u>

Line 23, delete the word "farther" and replace it with -- further --

<u>Column 10</u>

Line 42, delete the word "pin" and replace it with -- end --

Signed and Sealed this

Twenty-sixth Day of June, 2007

JON W. DUDAS
*Director of the United States Patent and Trademark Office*